(12) United States Patent
Sunkel et al.

(10) Patent No.: US 8,603,449 B2
(45) Date of Patent: Dec. 10, 2013

(54) RINSE-OFF CONDITIONING COMPOSITION COMPRISING A NEAR-TERMINAL BRANCHED ALCOHOL

(75) Inventors: Jorge Max Sunkel, Cincinnati, OH (US); Toshiyuki Iwata, Kobe (JP); Jeffrey John Scheibel, Loveland, OH (US); David Johnathan Kitko, Cincinnati, OH (US); Jun Xu, Mason, OH (US); Charles Winston Saunders, Fairfield, OH (US); Kenneth Nathan Price, Cincinnati, OH (US); Stephanie Ann Urbin, Cincinnati, OH (US); Phillip Richard Green, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 122 days.

(21) Appl. No.: 13/183,029

(22) Filed: Jul. 14, 2011

(65) Prior Publication Data

US 2012/0014901 A1 Jan. 19, 2012

Related U.S. Application Data

(60) Provisional application No. 61/364,519, filed on Jul. 15, 2010.

(51) Int. Cl.
*A61Q 5/12* (2006.01)
*A61Q 5/00* (2006.01)

(52) U.S. Cl.
USPC ..................................... 424/70.28; 424/70.12

(58) Field of Classification Search
None
See application file for complete search history.

(56) References Cited

U.S. PATENT DOCUMENTS

| | | | |
|---|---|---|---|
| 6,335,312 B1 | 1/2002 | Coffindaffer et al. | |
| 6,986,886 B2 * | 1/2006 | Hammond et al. | ........ 424/70.12 |
| 7,740,873 B2 | 6/2010 | Decoster et al. | |
| 8,147,813 B2 | 4/2012 | Beauquey et al. | |
| 8,349,301 B2 * | 1/2013 | Wells et al. | ................ 424/70.19 |
| 8,349,302 B2 * | 1/2013 | Johnson et al. | ............ 424/70.19 |
| 8,361,448 B2 * | 1/2013 | Johnson et al. | ............ 424/70.19 |
| 8,361,449 B2 * | 1/2013 | Wells et al. | ................ 424/70.19 |
| 2004/0076654 A1 | 4/2004 | Vinson et al. | |
| 2007/0298004 A1 | 12/2007 | Li | |
| 2009/0221463 A1 | 9/2009 | Kitko et al. | |
| 2011/0212043 A1 * | 9/2011 | Pham et al. | ................ 424/70.11 |
| 2012/0012130 A1 | 1/2012 | Hutton, III et al. | |
| 2012/0014900 A1 | 1/2012 | Carter et al. | |
| 2012/0014901 A1 | 1/2012 | Sunkel et al. | |

FOREIGN PATENT DOCUMENTS

JP 2000-344697 12/2000

OTHER PUBLICATIONS

PCT International Search Report and Written Opinion dated Mar. 22, 2013.

* cited by examiner

*Primary Examiner* — Jyothsna Venkat
(74) *Attorney, Agent, or Firm* — Angela K. Haughey

(57) ABSTRACT

A rinse-off conditioning composition comprising: (a) near-terminal branched alcohol according to Formula I; (b) a cationic surfactant; (c) a terminal aminosilicone; wherein the near-terminal branched alcohol and the cationic surfactant are comprised in a lamellar gel matrix.

3 Claims, 4 Drawing Sheets

RINSE-OFF CONDITIONING COMPOSITION COMPRISING A NEAR-TERMINAL BRANCHED ALCOHOL

CROSS REFERENCE TO RELATED APPLICATION

This application claims the benefit of U.S. Provisional Application No. 61/364,519, filed Jul. 15, 2010.

FIELD OF THE INVENTION

A rinse-off conditioning composition comprising: (a) near-terminal branched alcohol according to Formula I; (b) a cationic surfactant; (c) a terminal aminosilicone; wherein the near-terminal branched alcohol and the cationic surfactant are comprised in a lamellar gel matrix.

BACKGROUND OF THE INVENTION

Human hair becomes dry and/or damaged due to the surrounding environment, styling, regular cleansing, drying, and/or coloring or otherwise chemically treating the hair.

A variety of approaches have been developed to condition the hair. A common method of providing conditioning benefit is through the use of hair care compositions containing conditioning agents such as cationic surfactants and polymers, high melting point fatty compounds, low melting point oils, silicone compounds, and mixtures thereof. Silicones are often used as a conditioning active for a number of hair care compositions.

There is a constant need for providing conditioning compositions that can deposit an increased amount of silicone onto hair. Moreover, there is a need to providing conditioning compositions with excellent conditioning performance, but reduced stickiness and load on the hair. Finally, there is a need to find actives aiding conditioning which can be derived from natural and/or renewable sources.

The use of branched compounds in personal care compositions is known e.g. WO99/18929; WO2005/009385; U.S. Pat. No. 6,150,312; WO2009/090617; WO2009/053931. None of the existing art provides all of the advantages and benefits of the present invention.

SUMMARY OF THE INVENTION

According to a first aspect, rinse-off conditioning composition comprising:
(a) a near-terminal branched alcohol according to Formula I

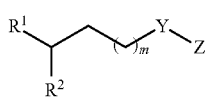

wherein $R^1$ is methyl, ethyl or propyl; $R^2$ is methyl; m is alkyl or alkenyl comprising a carbon chain of 5 to 19 carbons; Y is null or $W_p$; W is selected from the group consisting of ethyleneoxy, propylenoxy, butylenoxy, and mixtures thereof; p is 1 to 30; Z is hydroxyl;
(b) a cationic surfactant;
(c) a terminal aminosilicone;
wherein the near-terminal branched alcohol and the cationic surfactant are comprised in a lamellar gel matrix.

According to a second aspect, the present invention relates to the use of the composition according to the first aspect for depositing a terminal aminosilicone onto hair.

According to a third aspect, the present invention relates to a method of conditioning hair comprising applying the composition according to the first aspect onto hair.

DETAILED DESCRIPTION OF THE INVENTION

Figure 1:
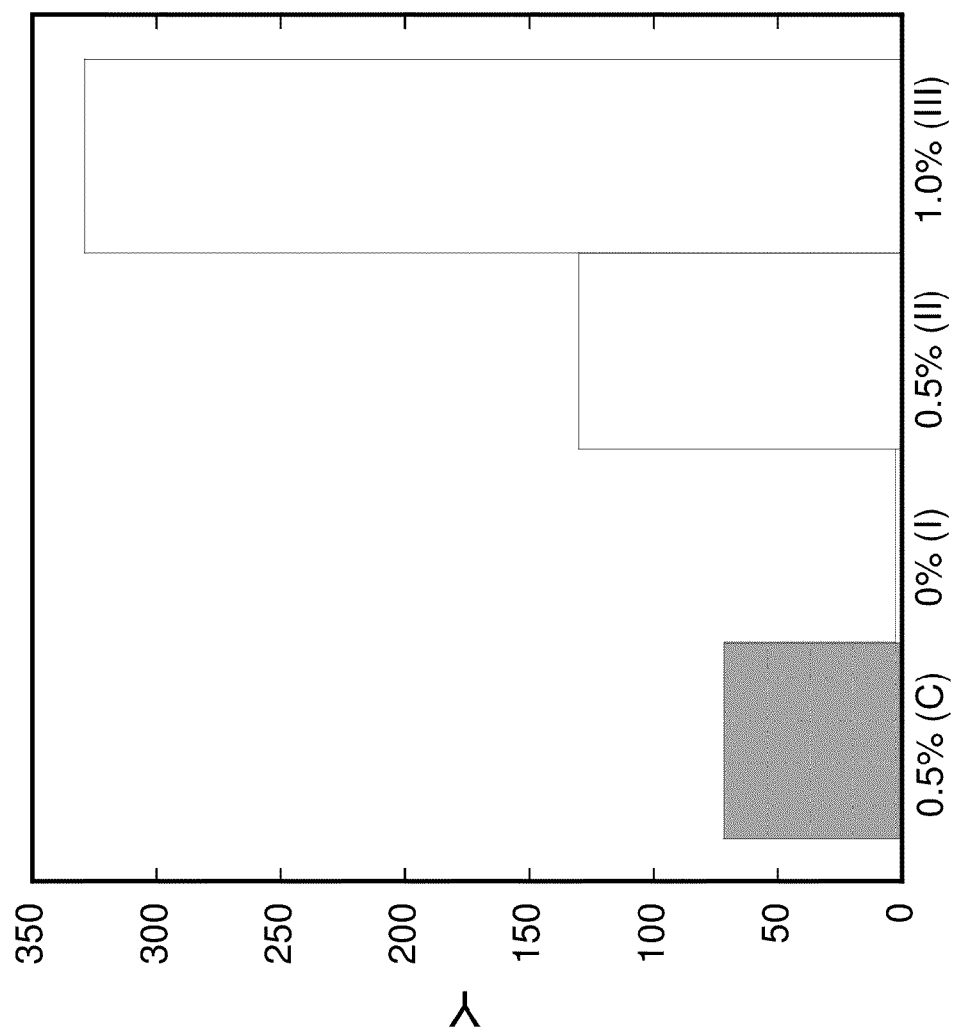
FIG. 1: Shows deposition of silicone onto hair, which had been treated with one of four different conditioning compositions. Y is the ppm of amodimethicone deposited per gram of hair. Sample C was treated with a control composition not per the present invention. Sample I is a terminal-aminosilicone-free control. Samples II to III were treated with different conditioning compositions both of which are pursuant to the present invention. The percentage indicated relates to the wt % of amodimethicone present in the conditioning composition.

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the number average molecular weight unless otherwise stated.

All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

Herein, "comprising" means that other steps and other ingredients which do not affect the end result can be added. This term encompasses the terms "consisting of" and "consisting essentially of". The compositions, methods, uses, kits, and processes of the present invention can comprise, consist of, and consist essentially of the elements and limitations of the invention described herein, as well as any of the additional or optional ingredients, components, steps, or limitations described herein.

The term "substantially free from" or "substantially free of" as used herein means less than about 1%, preferably less than about 0.8%, more preferably less than about 0.5%, still more preferably less than about 0.3%, most preferably about 0%, by total weight of the composition.

"Hair," as used herein, means mammalian hair including scalp hair, facial hair and body hair, more preferably hair on the human head and scalp.

As used herein, "near-terminal branched alcohol" contain 1, 2 or 3 ($C_1$-$C_3$)alkyl branches on a carbon atom within 40% of the non-functionalized end of the carbon backbone. The functionalized end of the near-terminal branched alcohol is the hydroxyl end. The non-functionalized carbon at the end of carbon backbone is referred to as the 'omega' position. For example, near-terminal branched alcohols that are 10 carbon atoms in length can have branching up to the omega-3 position, while near-terminal branched alcohols that are 30 carbon atoms in length can have branching up to the omega-11 position. The near-terminal branched alcohols of the invention typically have branching at the omega-1, omega-2, omega-3, omega-4, omega-5, and/or omega-6 positions of the compound (illustrated in the structure below), depending on the length of the compound, preferably at the omega-1, omega-2, and/or omega-3 positions, more preferably at the omega-1 and/or omega-2 positions.

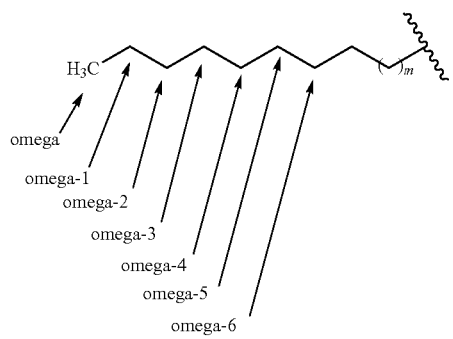

Near-terminal branched alcohols with branching at the omega-1 position are referred to as "iso". Near terminal-branched alcohols with branching at the omega-2 position are referred to as "anteiso". For example, an alcohol with 10 carbon atoms in its carbon backbone with a methyl branch at the omega-1 position: the branch is within 40% of the non-functionalized end of the carbon chain (e.g., 2/10× 100%=20%) and is referred to as near-terminal branched. Another example of a near-terminal branched alcohol is a alcohol with 10 carbon atoms in its carbon backbone and methyl substituent at the omega-3 position, which is within 40% of the non-functionalized end of the carbon chain (e.g., 4/10×100%=40%). In contrast, a alcohol with 10 carbon atoms in its carbon backbone and methyl branch at the omega-4 position—the branch is not within 40% of the non-functionalized end of the carbon chain (e.g., 5/10× 100%=50%) and so is not referred to as "near-terminal branched."

As used herein, the term "alkyl" refers to straight chained and branched saturated hydrocarbon groups, nonlimiting examples of which include methyl, ethyl, and straight and branched propyl, butyl, pentyl, hexyl, heptyl, and octyl groups containing the indicated number of carbon atoms. The term $C_n$ means the alkyl group has "n" carbon atoms. For example, ($C_1$-$C_7$)alkyl refers to an alkyl groups having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms).

As used herein, the term "alkenyl" is defined identically as "alkyl" except for containing a carbon-carbon double bond, e.g., ethenyl, propenyl, and butenyl.

As used herein, "linear compounds" e.g. "linear alcohols" are free of branches on the carbon backbone.

As used herein, "mid-chain" branched alcohols contain alkyl branches on a carbon atom that is between about 40% to about 60% of the non-functionalized end of the longest carbon backbone. For example, a mid-chain branched alcohol that is 12 carbon atoms in length can have branching on the omega-5 and/or omega-6 position. A mid-chain branched compound that is 30 carbon atoms in length can have branching on the omega-12 to the omega-17 position.

"Carbon backbone", as used herein, means the longest carbon chain in the compound.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, and/or alcohol derivatives of a given compound.

The inventors have surprisingly found that the rinse-off conditioning compositions pursuant to the present invention result in reduced static and kinetic friction of dry hair. Furthermore, an improved rinse profile and wet combing benefits are also exhibited by hair treated with the composition as described herein. Moreover a cleaner feel of the hair results. Furthermore, the compositions are stable at low temperatures and tolerate hard water conditions.

As shown by the figures, the present invention causes increased silicone deposition. The increased deposition of terminal aminosilicone is particularly important. 18-methyl eicosanoic acid (18-MEA) is a lipid naturally present on the outside of the hair cuticle, which lubricates the hair. 18-MEA is a carboxylic acid comprising 20 carbon atoms with a methyl group at the 18 position, which is the 2-omega or anteiso position. Without being bound by theory, the inventors believe that the near-terminal branched alcohol acts as a mimic of 18-MEA and thus 'top-up' the natural lubricant of the hair. Consequently the reduced friction benefits result when hair is treated with the present invention. The inventors believe that this is due to a reduction in surface energy (reduction in inter-fiber friction).

The first aspect relates to a rinse-off conditioning composition comprising: a near-terminal branched alcohol according to Formula I

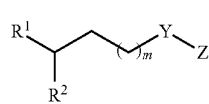

I wherein $R^1$ is methyl, ethyl or propyl; $R^2$ is methyl; m is alkyl or alkenyl comprising a carbon chain of 5 to 19 carbons; Y is null or $W_p$; W is selected from the group consisting of ethyleneoxy, propylenoxy, butylenoxy, and mixtures thereof; p is 1 to 30; Z is hydroxyl.

The near-terminal branched alcohol is comprised in a lamellar gel matrix. In other words, the composition comprises a lamellar gel matrix and the lamellar gel matrix comprises the near-terminal branched alcohol. The presence of a gel network or gel matrix can be can be measured by various test methods including SAXS and DSC (Differential Scanning calorimetry) analytical test methods.

The composition may comprise from about 0.05% to about 5.0%, or from about 0.075% to about 4.5%, or from about 0.1% to about 4.0%, of the near-terminal branched alcohol by total weight of the composition.

In an embodiment, m comprises a carbon chain of 7 to 19, preferably is 9 to 19, more preferably 11 to 18, most preferably 12 to 17 carbons; and Y is null. In another embodiment, m comprises a saturated carbon chain. In another embodiment, the carbon chain of m comprises 1 to 3 branches wherein each branch is selected from the group consisting of methyl, ethyl and propyl. The near-terminal branched alcohol may be selected from the group consisting of 4,8,12-trimethyl-1-tridecanol, 3-ethyl-7,11-dimethyl-1-dodecanol, 11-methyldodecanol, 10-methyldodecanol, 15-methylhexadecanol, 14-methylhexadecanol, and 16-methylheptadecanol, 15-methylheptadecanol, 17-methyloctadecanol, 16-methyloctadecanol, 21-methyldocosanol, 20-methyldocosanol, 12-methyltetradecan-1-ol, 12-methyltridecane-1-ol and 11-methyltetradecan-1-ol, and mixtures thereof.

The composition may comprise at least two near-terminal branched alcohols as defined herein. In an embodiment, the composition comprises at least two near-terminal branched alcohols selected from the group consisting of 4,8,12-trimethyl-1-tridecanol, 3-ethyl-7,11-dimethyl-1-dodecanol, 11-methyldodecanol, 10-methyldodecanol, 15-methylhexadecanol, 14-methylhexadecanol, and 16-methylheptadecanol, 15-methylheptadecanol, 17-methyloctadecanol, 16-methyloctadecanol, 21-methyldocosanol, 20-methyldocosanol, 12-methyltetradecan-1-ol, 12-methyltridecane-1-ol, 11-methyltetradecan-1-ol, and mixtures thereof.

In an embodiment, the composition comprises near-terminal branched alcohols selected from the group consisting of: two iso alcohols, two anteiso alcohols, and one iso alcohol and one anteiso alcohol.

In an embodiment, the near-terminal branched alcohol is synthesized by metathesis. See synthesis mechanisms below. In an embodiment, at least 50%, or at least 60%, or at least 70%, or at least 85% of said near-terminal branched alcohol is derived from natural feedstocks. In an embodiment, at least 50% of said near-terminal branched alcohol is not derived from petroleum.

In an embodiment, the composition comprises a further branched alcohol, which is selected from the group consisting of: near-terminal branched alcohol; mid-chain branched alcohol; and mixtures thereof. In an embodiment, the further branched alcohol is a near-terminal branched compound. In an embodiment, the further branched alcohol comprises at least one branch located at a position selected from the group consisting of: omega-1, omega-2, omega-3, omega-4, omega-5, and omega-6; or omega-1, omega-2, and omega-3; or omega-1 and omega-2. In an embodiment, the further branched alcohol comprises only one branch, wherein the branch is located at a position selected from the group consisting of: omega-1, omega-2, and omega-3; or omega-1 and omega-2. The composition may be substantially free of any branched compound that is neither a near-terminal branched alcohol nor mid-chain branched alcohol. In an embodiment, the composition is substantially free of a mid-chain branched compound.

The composition comprises a cationic surfactant. The composition may comprise from about 0.05% to about 3.0%, or from about 0.075% to about 2.0%, or from about 0.1% to about 1.0%, of cationic surfactant by total weight of the composition. The cationic surfactant is comprised in a lamellar gel matrix. In other words, the composition comprises a lamellar gel matrix and the lamellar gel matrix comprises the cationic surfactant.

In an embodiment, cationic surfactant is according to Formula II

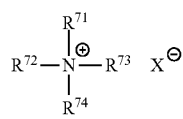

wherein at least one of $R^{71}$, $R^{72}$, $R^{73}$ and $R^{74}$ is selected from: an aliphatic group of from 8 to 30 carbon atoms; an aromatic, alkoxy, polyoxyalkylene, alkylamido, hydroxyalkyl, aryl; or an alkylaryl group having up to 22 carbon atoms;

the remainder of $R^{71}$, $R^{72}$, $R^{73}$ and $R^{74}$ are independently selected from the group consisting of: an aliphatic group consisting of from 1 to 22 carbon atoms; and an aromatic, alkoxy, polyoxyalkylene, alkylamido, hydroxyalkyl, aryl or alkylaryl group having up to 22 carbon atoms;

X is selected from the group consisting of: halogen, acetate, citrate, lactate, glycolate, phosphate, nitrate, sulfonate, sulfate, alkylsulfate, alkyl sulfonate radicals, and mixtures thereof.

The cationic surfactant may be selected from the group consisting of: behenyl trimethyl ammonium chloride, methyl sulfate or ethyl sulfate, and stearyl trimethyl ammonium chloride, methyl sulfate or ethyl sulfate. It is believed that a longer alkyl group provides improved smoothness and soft feeling on wet and dry hair, compared to cationic surfactants with a shorter alkyl group. It is also believed that such cationic surfactants can provide reduced irritation, compared to those having a shorter alkyl group.

The cationic surfactant may be a di-long alkyl quaternized ammonium salt selected from the group consisting of: dialkyl (14-18) dimethyl ammonium chloride, disallow alkyl dimethyl ammonium chloride, dihydrogenated tallow alkyl dimethyl ammonium chloride, distearyl dimethyl ammonium chloride, dicetyl dimethyl ammonium chloride, and mixtures thereof.

In an embodiment, the cationic surfactant is a tertiary amido amine having an alkyl group of from about 12 to about 22 carbons. The tertiary amido amine may be selected from the group consisting of stearamidopropyldimethyl-, stearamidopropyldiethyl-, stearamidoethyldiethyl-, stearamidoethyldimethyl-, palmitamidopropyldimethyl-, palmitamidopropyldiethyl-, palmitamidoethyldiethyl-, palmitamidoethyldimethyl-, behenamidopropyldimethyl-, behenamidopropyldiethyl-, behenamidoethyldiethyl-, behenamidoethyldimethyl-, arachidamidopropyldimethyl-, arachidamidopropyldiethyl-, arachidamidoethyldiethyl-, and arachidamidoethyldimethyl-amine, diethylaminoethylstearamide, and mixtures thereof.

A tertiary amido amine may be used in combination with an acid. The acid is typically used as a salt-forming anion. In an embodiment, the acid is selected from the group consisting of: lactic acid, malic acid, hydrochloric acid, 1-glumatic acid, acetic acid, citric acid, and mixtures thereof.

In an embodiment, the cationic surfactant is selected from the group consisting of: cetyltrimonium chloride (CTAC), stearyltrimonium chloride (STAC), behentrimonium methosulfate, stearoylamidopropyldimethyl amine (SAPDMA), distearyldimethylammonium chloride, and mixtures thereof.

The composition comprises a terminal aminosilicone. "Terminal aminosilicone" as defined herein means silicone comprising one or more amino groups at one or both ends of the silicone backbone. In an embodiment, the composition is substantially free of any silicone compound comprising pendant amino groups. In an embodiment, the composition is substantially free of any silicone compound other than terminal aminosilicones. In an embodiment, the amino group at least one terminus of the silicone backbone of the terminal aminosilicone is selected from the group consisting of: primary amines, secondary amines and tertiary amines. The terminal aminosilicone may conform to Formula III:

$$(R_1)_a G_{3-a}\text{-Si}-(-OSiG_2)_n-O-SiG_{3-a}(R^1)_a \qquad \text{III}$$

wherein G is hydrogen, phenyl, hydroxy, or $C_1$-$C_8$ alkyl, preferably methyl; a is an integer having a value from 1 to 3, preferably 1; b is 0, 1 or 2, preferably 1; n is a number from 0 to 1,999; $R_1$ is a monovalent radical conforming to the general formula $CqH_{2q}L$, wherein q is an integer having a value from 2 to 8 and L is selected from the following groups: $-N(R_2)CH_2-CH_2-N(R_2)_2$; $-N(R_2)_2$; $-N(R_2)_3A^-$; $-N(R_2)CH_2-CH_2-NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion.

A suitable terminal aminosilicone corresponding to Formula III has a=1, q=3, G=methyl, n is from about 1000 to about 2500, alternatively from about 1500 to about 1700; and L is $-N(CH_3)_2$. A suitable terminal aminosilicone corresponding to Formula III has a=0, G=methyl, n is from about 100 to about 1500, or from about 200 to about, L is selected from the following groups: $-N(R_2)CH_2-CH_2-N(R_2)_2$; $-N(R_2)_2$; $-N(R_2)_3A^-$; $-N(R_2)CH_2-CH_2-NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion, alternatively L is $-NH_2$. In an embodiment, the terminal aminosilicone is selected from the group consisting of bis-aminomethyl dimethicone, bis-aminoethyl dimethicone, bis-aminopropyl dimethicone, bis-aminobutyl dimethicone, and mixtures thereof. In an embodiment, the viscosity of the terminal aminosilicone is from about 1,000 to about 30,000 cPs, or from about 5,000 to about 20,000 cPs measured at 25° C.

The composition may comprise from about 0.1% to about 20%, or from about 0.5% to about 10%, or from about 1% to about 6% terminal aminosilicone, by total weight of the composition. In an embodiment, the weight ratio of total near-terminal branched alcohol to terminal aminosilicone is from about 0.5:1 to about 6:1, or from about 1:1 to about 4:1. In an embodiment, the lamellar gel matrix does not comprise the terminal aminosilicone.

In embodiment, lamellar gel matrix comprises the cationic surfactant, the near-terminal branched alcohol and a high melting point fatty compound. In view of providing the above lamellar gel matrix, the cationic surfactant and the high melting point fatty compound are contained at a level such that the weight ratio of the cationic surfactant to the high melting point fatty compound is in the range of, or from about 1:1 to about 1:10, or from about 1:1 to about 1:6.

The high melting point fatty compound useful herein has a melting point of 25° C. or higher, and is selected from the group consisting of a fatty alcohol, fatty acid, fatty alcohol derivative, fatty acid derivative, and mixtures thereof. Non-limiting examples of the high melting point compounds are found in International Cosmetic Ingredient Dictionary, Fifth Edition, 1993, and CTFA Cosmetic Ingredient Handbook, Second Edition, 1992. The composition may comprise from about 0.1% to about 40%, or from about 1% to about 30%, or from about 1.5% to about 16%, or from about 1.5% to about 8% of a high melting point fatty compound, by total weight of the composition, in view of providing improved conditioning benefits such as slippery feel during the application to wet hair, softness and moisturized feel on dry hair.

In an embodiment, fatty alcohol is selected from the group consisting of: cetyl alcohol, stearyl alcohol, behenyl alcohol, and mixtures thereof. In an embodiment, the composition comprises a linear fatty alcohol, wherein the linear fatty alcohol is also comprised in the lamellar gel matrix. The lamellar gel matrix is suitable for providing various conditioning benefits such as slippery feel during the application to wet hair and softness and moisturized feel on dry hair. The linear fatty alcohol may comprise from 8 to 24 carbon atoms. In an embodiment, the linear fatty alcohol is selected from the group consisting of: cetyl alcohol, stearyl alcohol, and mixtures thereof. In an embodiment, the weight ratio of total linear fatty alcohol to terminal aminosilicone is from about 0.5:1 to about 10:1, or from about 1:1 to about 5:1, or from about 2.4:1 to about 2.7:1.

The composition may be in the form of a pourable liquid (pourable when under ambient conditions). In an embodiment the composition comprises a cosmetically acceptable aqueous carrier and is in the form of a pourable liquid. The composition may comprise a cosmetically acceptable aqueous carrier present at a level of from about 20% to about 95%, or from about 60% to about 85%. The cosmetically acceptable aqueous carrier may be selected from the group consisting of water and water solutions of lower alkyl alcohols and polyhydric alcohols. The lower alkyl alcohols may be monohydric alcohols having 1 to 6 carbons. In an embodiment, the lower alkyl alcohols are ethanol and isopropanol. The polyhydric alcohols may be propylene glycol, hexylene glycol, glycerin, and propane diol.

The composition may further comprise: water soluble vitamins and their derivatives, water soluble amino acids and their salts and/or derivatives, viscosity modifiers, dyes, nonvolatile solvents or diluents (water soluble and insoluble), pearlescent aids, thickeners, foam boosters, additional surfactants or nonionic co-surfactants, pediculocides, pH adjusting agents, perfumes, preservatives, chelants, proteins, skin active agents, sunscreens, UV absorbers, vitamins, niacinamide, caffeine and minoxidil. The composition may comprise from about 0% to about 5% vitamins and amino acids, by total weight of the composition. The composition may also comprise pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocyanine, botanical, natural colors, including: water soluble components such as those having C.I. Names. The composition may comprise from about 0% to about 5% pigment materials. The composition may comprise from about 0% to about 5% antimicrobial agents. The composition may have a pH of from about 6 to about 10, or from about 7 to about 10, or from about 7 to about 9.

In an embodiment, the composition is for depositing a terminal aminosilicone onto hair, or for providing improved deposition of the terminal aminosilicone onto hair.

The second aspect relates to the use of the composition according to the first aspect for depositing a terminal aminosilicone onto hair, or providing improved deposition of a terminal aminosilicone onto hair. The terminal aminosilicone is described herein.

The third aspect relates to a method of conditioning hair comprising applying the composition according to the first aspect onto hair.

Synthesis Mechanism

The branched alcohols may be synthesized by metathesis. Useful mechanisms are also discussed in Suguro and Mori (1979), *Agric. Biol. Chem.,* 43 (4), 869; Yuasa and Tsuruta (2004), *Flavour Fragr. J.,* 19, 199. Furthermore, production via genetically engineered bacteria is described in US2010/0105955; US2010/0105963; WO2007/136752; WO2008/119082; WO2009/111672; and US61/289,039.

Metathesis of Glyceryl Trioleate with 3-Methyl-1-Hexene, 4-Methyl-1-Hexene and 4-Methyl-1-Pentene to Prepare Near Terminal Branched Alcohols Reactants and subsequent products thereof can be derived from the oils: trioleate (shown in Scheme 1), soybean (hydrogenated), rapeseed, canola, palm, palm kernel, coconut, jatropha, high erucic rapeseed, cottonseed, tallow, yellow grease, corn, sunflower, babasu, and mixtures thereof. The olefin used in the metathesis reaction can be a single branched olefin, a mixture of branched olefins or a mixture of branched olefins with other nonreactive impurities such as aromatic alkyls, paraffins, branched paraffins and cycloalkanes.

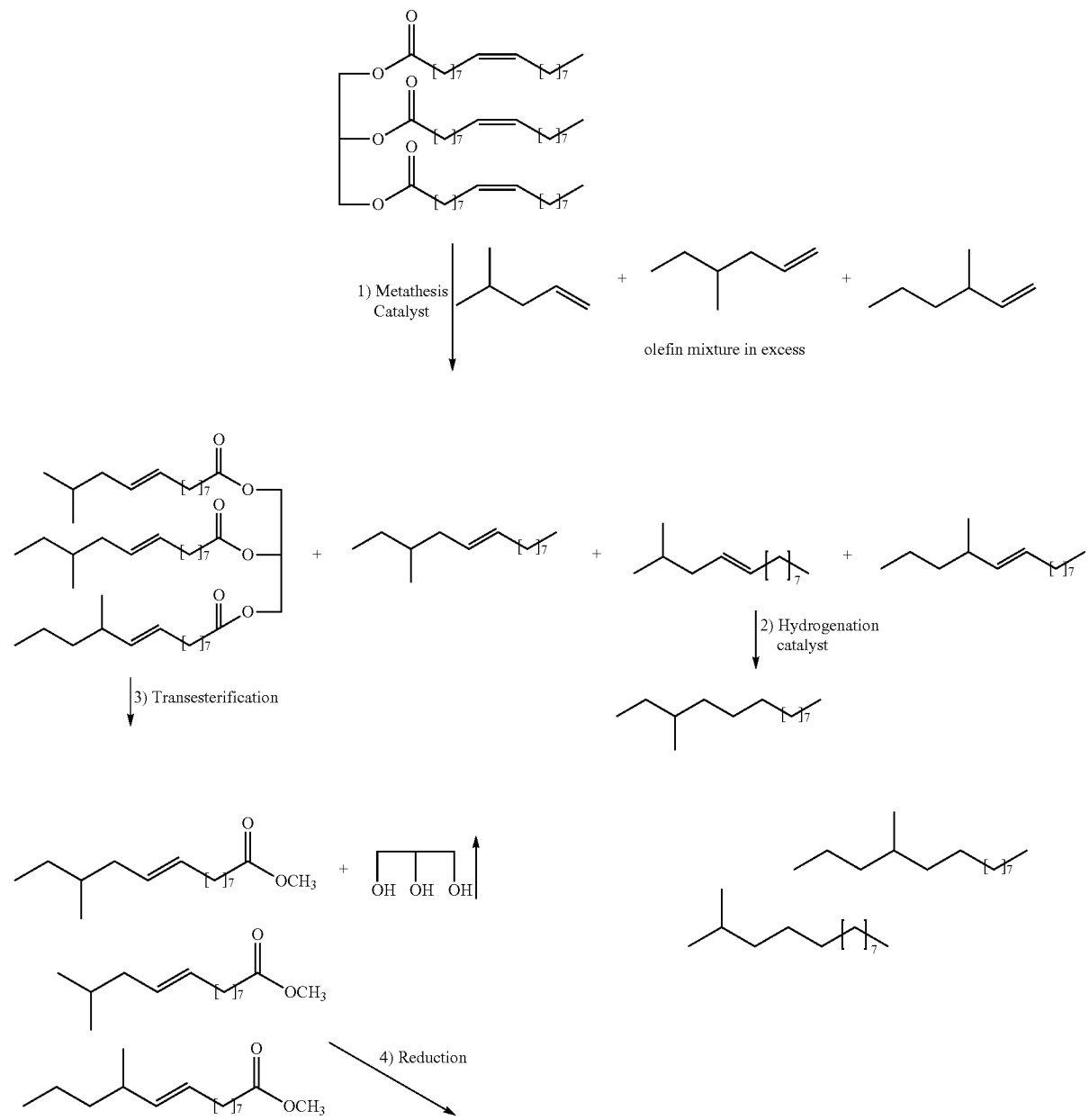

Scheme 1.

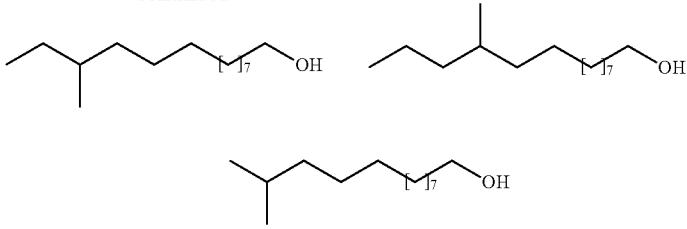

I.A. Synthesis of Mixture of Near Terminal-Branched Alcohols

About 8.854 g (0.010 mol) of glyceryl trioleate (Sigma catalog #T7140) and 25 mL of hexane are placed in a 316 stainless steel stirred pressure vessel. Solvent and glycerol trioleate are predried over 4 Å molecular sieves prior to introduction to vessel. About 0.0006 mol of tungsten hexachloride and 0.0006 mol of tetramethyl tin is added to the vessel. The reactor is sealed, stirred, and purged several times with $N_2$. About 0.030 mol of a blend of 3-methyl-1-hexene, 4-methyl-1-hexene and 4-methyl-1-pentene is added to the vessel under $N_2$. The stirred mixture is heated to 220° C. under 100 psig $N_2$ and maintained at this temperature for several hours. The reactor is cooled and the product removed. The reaction mixture is quenched with 2-3 mL of concentrated ammonium hydroxide and extracted with additional 10 mL hexane. The hexane and any volatile olefins remaining are stripped on a rotary evaporator. The remaining product is subjected to fractional distillation to remove the remaining non volatile olefin mixture. This branched olefin mixture containing mainly a mixture of 11-methyl-9-tetradecene, 12-methyl-9-tridecene and 12-methyl-9-tetradecene is hydrogenated under standard reaction conditions to provide a high quality semi-biodiesel fuel with branching. The bottom of the flask from distillation contains mainly the new branched triglyceride mixture. This new triglyceride mixture is subjected to standard transesterification conditions in the presence of methanol and a catalytic amount of sodium hydroxide or sodium methoxide in methanol. The mixture phase separates into glycerine (bottom phase) and a mixture of methyl esters (top phase) consisting mainly of 12-methyl-9-tetradecenoic acid methyl ester, 12-methyl-9-tridecenoic acid methyl ester and 11-methyl-9-tetradecenoic acid methyl ester. The unique branched methyl ester mixture is reduced using standard procedures with copper chromite catalyst in the presence of hydrogen to give essentially a mixture of 12-methyltetradecan-1-ol, 12-methyltridecane-1-ol and 11-methyltetradecane-1-ol. The mixture is vacuum distilled to provide a purified mixture.

I.B. Near Terminal Branched Alcohol Ethoxylate 223.7 grams (1.0 mol) of the near terminal alcohol mixture of Example I.A. above plus sufficient catalyst to facilitate the reaction of the alcohol with ethylene oxide within a suitable period of time and in a controllable manner are charged to a 600 mL stainless steel stirred pressure vessel with a cooling coil. A suitable catalyst is 1.1 grams of a solution consisting of 50% potassium hydroxide in water. Other kinds and quantities of catalyst can be used. The reactor is heated while applying a vacuum for removing materials that can result in side products, such as water, that may be introduced with the catalyst, at a temperature that does not allow the loss of the near terminal alcohol mixture of example I.A., generally between 40° C. and 90° C., but preferably between about 60° C. and about at 80° C., when using a water aspirator as a vacuum source. The removal of water is facilitated by using low speed agitation, generally about 50 rpm, while sparging the mixture with a low level (trickle) stream of inert gas either through a bottom drain valve or through a stainless steel gas dispersion frit or any inert dip-tube or sintered metal fritted material or by sweeping the area above the mixture with inert gas. Samples can be drawn from the reactor and analyzed for water content using an appropriate analytical method such as Karl-Fischer titration. After completion of the water removal step, ethylene oxide can be added all at once if the reactor system is properly designed to prevent an uncontrolled rate of reaction. However, the best reaction control is obtained by first heating the reactor under a static vacuum (or optionally with added pressure from an inert gas such as $N_2$) to a temperature that is suitable for the reaction of the alcohol-catalyst mixture with ethylene oxide to occur with minimum side products and color generation, generally between 85° and 150° C., but preferably between about 110° C. and 130° C. Once the reactor has reached the desired temperature, 308 grams (7.0 mol) of ethylene oxide is added at a rate that will be controllable by the cooling system, generally over a period of 30 to 60 minutes. After the addition of ethylene oxide is completed, stirring and heating is continued until the ethylene oxide has been consumed by the reaction. The product can then be degassed and removed from the reaction vessel and stored as is or for long term storage the catalyst is neutralized with one equivalent of an acid selected from citric, HCl or sulfuric acid. The neutralized product can be filtered to remove any solid residue.

EXAMPLES

| Component | A | B | C | D | E | F |
|---|---|---|---|---|---|---|
| Water | QSP | QSP | QSP | QSP | QSP | QSP |
| VARISOFT ® 432PPG [1], quaternary ammonium di-alkyl solution | — | — | — | 0.5 | 0.5 | 0.5 |
| Behentrimonium Methosulfate/IPA | 2.2 | 2.2 | 2.2 | 1.4 | 1.4 | 1.4 |
| Ethylenediaminetetraacetic acid (EDTA) | 0.12 | 0.12 | 0.12 | 0.13 | 0.13 | 0.13 |
| 14-Methylhexadecanol | 0.75 | — | 0.75 | 0.45 | — | 0.45 |
| 15-Methylhexadecanol | 0.75 | 0.75 | — | 0.45 | 0.45 | — |

-continued

| Component | A | B | C | D | E | F |
|---|---|---|---|---|---|---|
| 15-Methylheptadecanol* | — | 0.75 | 0.75 | — | — | — |
| 16-Methyloctadecanol | — | — | — | — | 0.45 | 0.45 |
| Stearyl Alcohol | 3.7 | 3.7 | 3.7 | 2.3 | 2.3 | 2.3 |
| Benzyl Alcohol | 0.4 | 0.4 | 0.4 | 0.4 | 0.4 | 0.4 |
| Preservative (e.g., KATHON ™ CG [2]) | 0.03 | 0.03 | 0.03 | 0.03 | 0.03 | 0.03 |
| Amodimethicone [#] | 0.5 | 0.5 | 0.5 | 0.8 | 0.8 | 0.8 |
| Panthenol | 0.1 | 0.1 | 0.1 | 0.1 | 0.1 | 0.1 |
| Perfume | 0.4 | 0.4 | 0.4 | 0.3 | 0.3 | 0.3 |

KEY:
* = Derivable from metathesis of erucic acid-based triglyceride and 3-methyl-1-pentene;
[#] = a terminal aminosilicone;
QSP = sufficient quantity for 100%;
[1] = Dicetyldimonium chloride (~68% active) in propylene glycol and water;
[2] = blend of methylchloroisothiazolinone and methylisothiazolinone; numbers without units are in wt %.

Comparative Data

Experiment 1

Deposition of Conditioner Materials on Hair Switches

Clean, wet hair switches are treated with conditioner 1 samples at 0.1 g per gram of hair. The hair switches are rinsed with warm water and analysed for silicone deposition. Silicone deposition can be measured by Inductively Coupled Plasma Optical Emission Spectroscopy (ICP-OES). Silicone is extracted from hair samples with 50:50 toluene:methylisobutyl ketone and the extracted samples were compared to ICP calibration standards of known silicone concentration.

| | Conditioner 1 | | | |
|---|---|---|---|---|
| Ingredients (wt %) | C (Control) | I | II | III |
| Water (Distilled) | QSP | QSP | QSP | QSP |
| Behentrimonium methosulfate (BTMS) | 2.25 | 2.25 | 2.25 | 2.25 |
| Varisoft ® 432 PPG [1] | — | — | — | — |
| Disodium EDTA | 0.13 | 0.13 | 0.13 | 0.13 |
| 4, 8, 12-trimethyl-1-tridecanol | — | 1.49 | 1.49 | 1.49 |
| Stearyl Alcohol | 3.71 | 3.71 | 3.71 | 3.71 |
| Cetyl Alcohol | 1.486 | — | — | — |
| Benzyl Alcohol | 0.4 | 0.4 | 0.4 | 0.4 |
| Kathon ™ CG [2] | 0.033 | 0.033 | 0.033 | 0.033 |
| Amodimethicone [#] | 0.5 | — | 0.5 | 1 |

KEY: as for examples table above.

Data resultant from experiment 1 are found in FIG. 1. Conclusions: deposition of amodimethicone of Conditioner 1 (II) comprising 4,8,12-trimethyl-1-tridecanol and 0.5% amodimethicone is about twice as much as the control, which comprises 0.5% amodimethicone. Deposition of amodimethicone from Conditioner 1 (III) with 1% amodimethicone is very high relatively speaking.

Experiment 2

Deposition of Conditioner Materials on Hair Switches

Clean, wet hair switches are treated with conditioner 2 samples at 0.1 g per gram of hair. Hair switches are rinsed with warm water and analysed for silicone deposition.

| | Conditioner 2 | | |
|---|---|---|---|
| Ingredients (wt %) | C (Control) | I | II |
| Water (Distilled) | QSP | QSP | QSP |
| Behentrimonium methosulfate (BTMS) | 1.43 | 1.43 | 1.43 |
| Varisoft ® 432 PPG [1] | 0.50 | 0.50 | 0.50 |
| Disodium EDTA | 0.13 | 0.13 | 0.13 |
| 4, 8, 12-trimethyl-1-tridecanol | — | 0.93 | 0.93 |
| Stearyl Alcohol | 2.32 | 2.32 | 2.32 |
| Cetyl Alcohol | 0.93 | — | — |
| Benzyl Alcohol | 0.40 | 0.40 | 0.40 |
| Kathon ™ CG [2] | 0.03 | 0.03 | 0.03 |
| Amodimethicone [#] | 0.75 | 0.50 | — |

KEY: as for examples table above.

Figure 2:
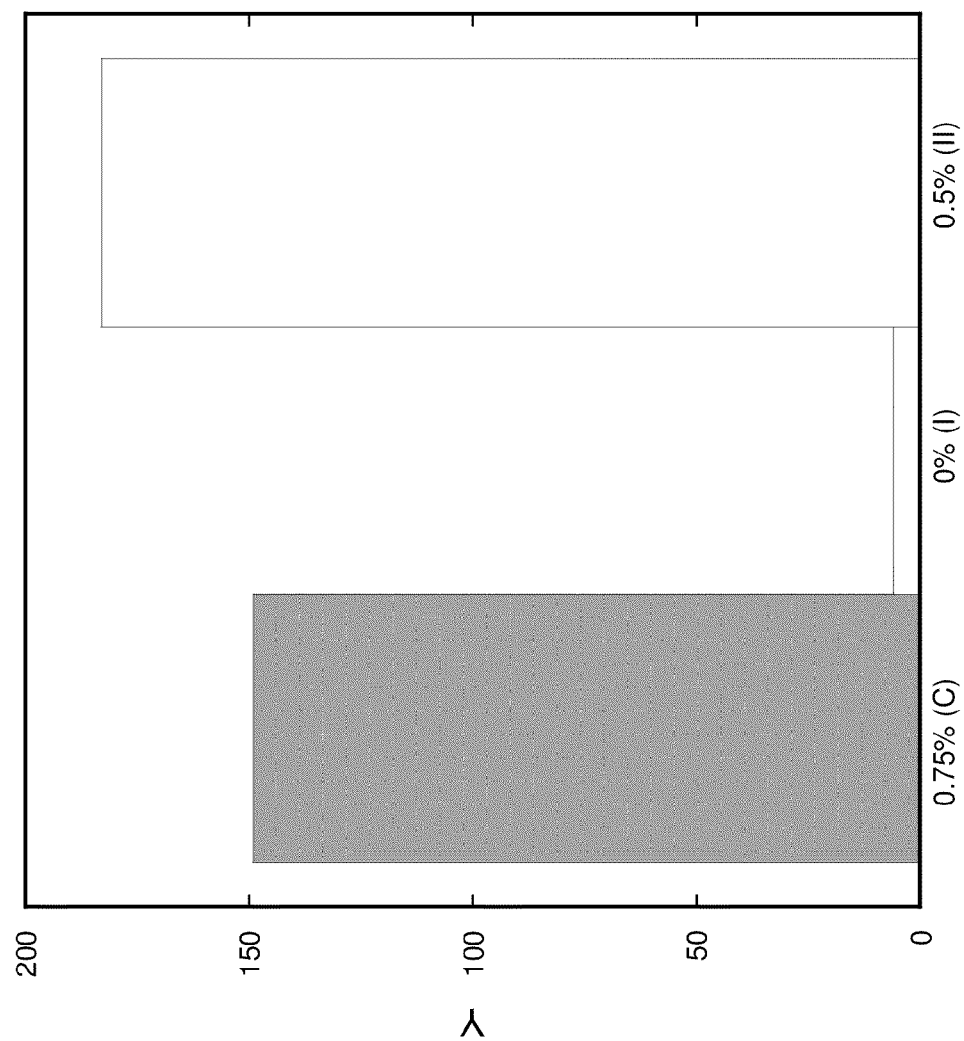
FIG. 2: Shows deposition of silicone onto hair, which had been treated with one of three different conditioning compositions. Y is the ppm of amodimethicone deposited per gram of hair. Sample C was treated with a control composition not per the present invention. Sample II is a terminal-aminosilicone free control. Sample I was treated with a conditioning composition pursuant to the present invention. The percentage indicated relates to the wt % of amodimethicone present in the composition.

Data resultant from Experiment 2 are found in FIG. 2. Conclusions: deposition of amodimethicone of Conditioner 2 (II) with 4,8,12-trimethyl-1-tridecanol and 0.5% amodimethicone significantly greater than the control containing 50% more (0.75%) amodimethicone. Relative to the low level of amodimethicone (0.5%) Conditioner 2 (II) is displays high/efficient amodimethicone deposition.

Experiment 3

Instron Kinetic Friction Measurement

Clean and wet hair switches are treated with conditioner as per the below table. The conditioner sample is then rinsed from the hair and dried. Kinetic friction is then measured with an Instron device. The kinetic friction measurement system measures the dynamic tension while the sled moves across the hair switch surface, which calculates the average of tension after 15 mm extension of sled movement. The switches are placed on a flat, horizontal surface and a 200 g sled (with black pad form) is pulled over the switch while measuring the force required to move it at a constant speed. Each experiment is performed in triplicate. Lower force implies better conditioning.

| | Conditioner 3 | |
|---|---|---|
| Ingredients (wt %) | C (Control) | I |
| Water (distilled) | QSP | QSP |
| Behentrimonium methosulfate (BTMS) | 1.43 | 1.43 |
| Varisoft ® 432 PPG [1] | 0.50 | 0.50 |

-continued

Conditioner 3

| Ingredients (wt %) | C (Control) | I |
|---|---|---|
| Disodium EDTA | 0.13 | 0.13 |
| 14-methyl-1-hexadecanol | — | 0.93 |
| Stearyl Alcohol | 2.32 | 2.32 |
| Cetyl Alcohol | 0.93 | — |
| Benzyl Alcohol | 0.40 | 0.40 |
| Kathon ™ CG [2] | 0.03 | 0.03 |
| Amodimethicone [#] | 0.75 | 0.75 |

KEY: as for examples table above.

Figure 3:
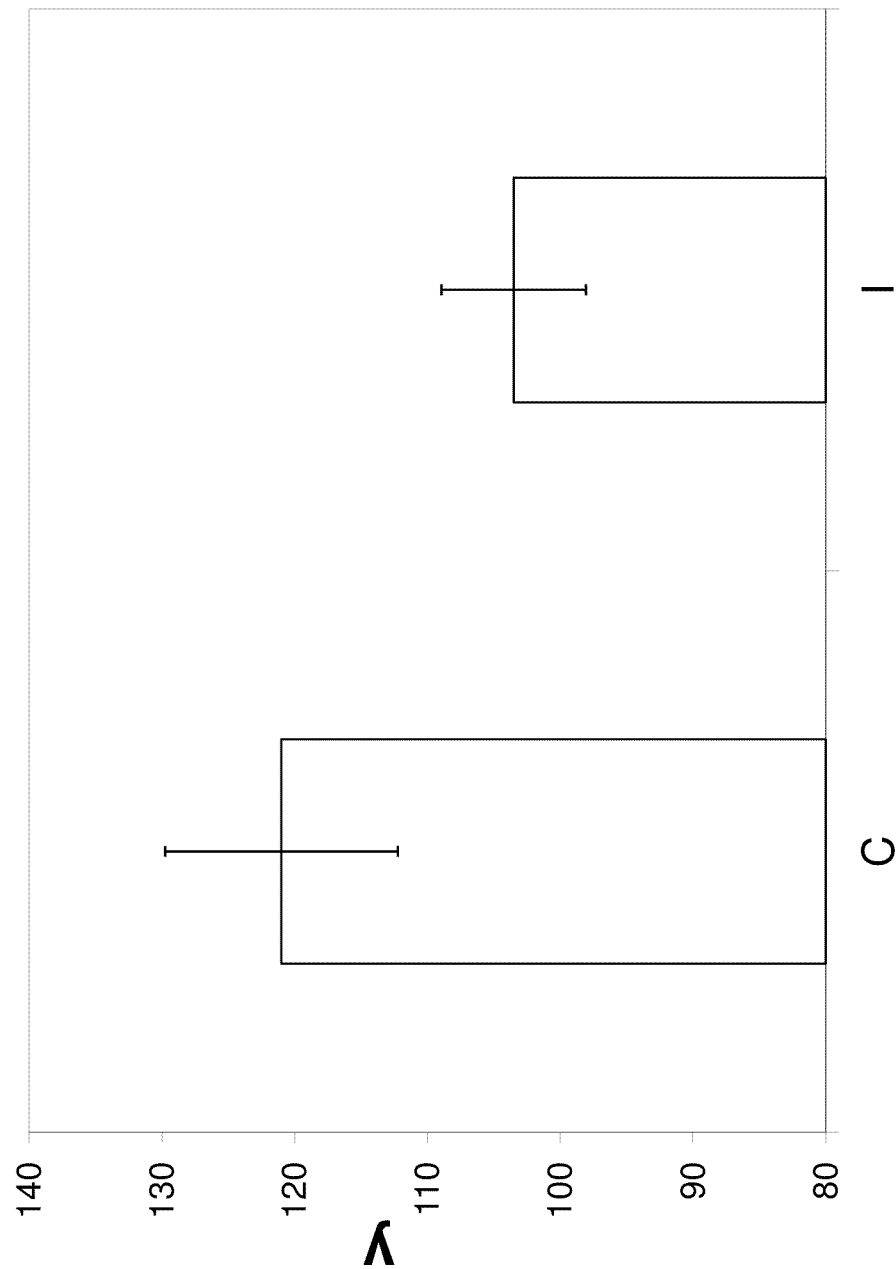
FIG. 3: Shows measurements of kinetic friction of hair, which had been treated with one of two different conditioning compositions. y is grams of force measured. Sample C was treated with a control composition not per the present invention. Sample I was treated with a conditioning composition pursuant to the present invention.
Figure 4:
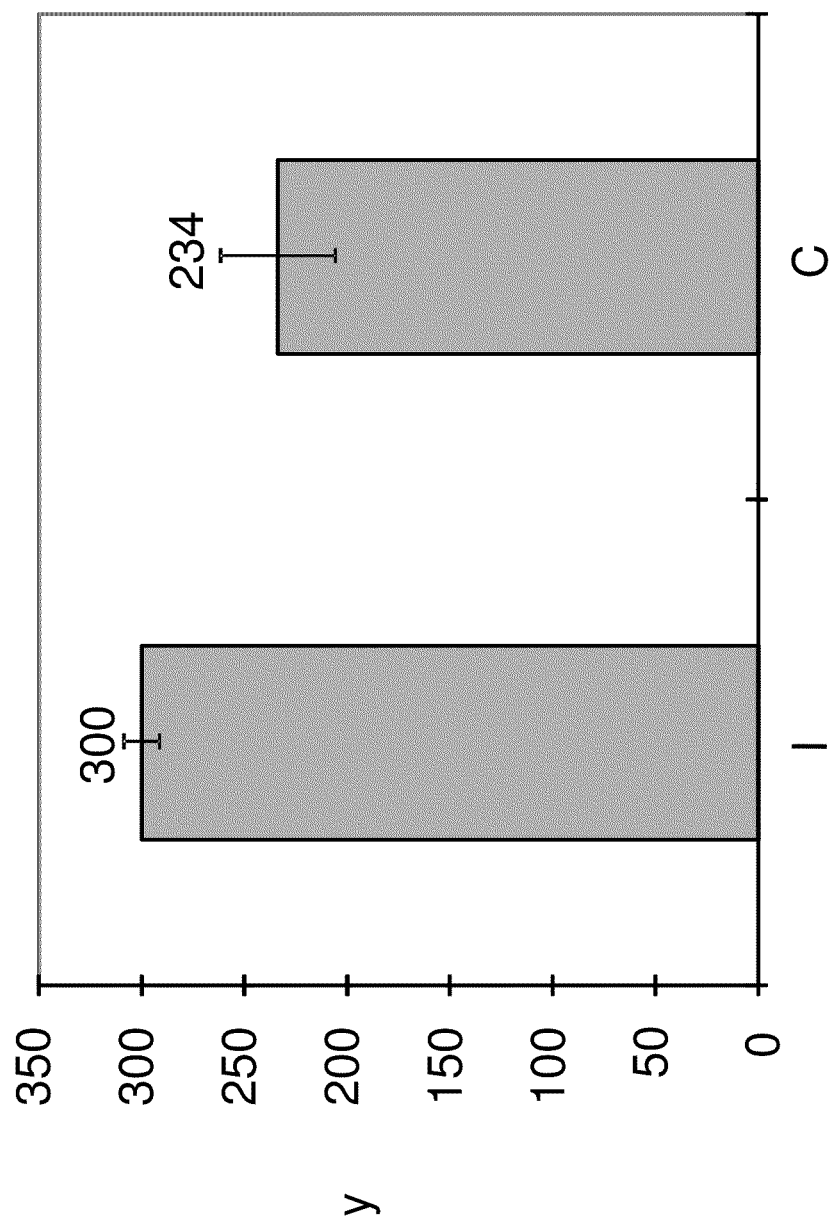
FIG. 4: Shows deposition of silicone onto hair, which had been treated with one of two different conditioning compositions. Y is the ppm of amodimethicone deposited per gram of hair. Sample C was treated with a control composition not per the present invention. Sample I was treated with a conditioning composition pursuant to the present invention.

Data resultant from experiment 3 are found in FIG. 3. Conclusions: sample I has lower friction versus the control. The same samples as described in Experiment 3 and the Conditioner 3 table were also used for silicone deposition measurements. Data resultant from this are found in FIG. 4.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

What is claimed is:

1. A rinse-off conditioning composition comprising: a lamellar gel matrix consisting of
   (a) from about 0.05% to about 5.0% by total weight of the composition a near-terminal branched alcohol selected from the group consisting of 4,8,12-trimethyl-1-tridecanol, 3-ethyl-7,11-dimethyl-1-dodecanol, 11-methyldodecanol, 10-methyldodecanol, 15-methylhexadecanol, 14-methylhexadecanol, 16-methylheptadecanol, 15-methylheptadecanol, 17-methyloctadecanol, 16-methyloctadecanol, 21-methyldocosanol, 20-methyldocosanol, 12-methyltetradecan-1-ol, 12-methyltridecan-1-ol, 11-methyltetradecan-1-ol, and mixtures thereof
   (b) from about 0.05% to about 3.0% by total weight of the composition a cationic surfactant selected from the group consisting of cetyltrimonium chloride, stearyltrimonium chloride, behentrimonium methosulfate, distearyldimethylammonium chloride, and mixtures thereof
   (c) from about 0.1% to about 40.0% by total weight of the composition a linear fatty alcohol selected from the group consisting of cetyl alcohol, stearyl alcohol, behenyl alcohol, and mixtures thereof
   (d) and a cosmetically acceptable carrier
   and from about 0.1% to about 20.0% by total weight of the composition a terminal amino silicone selected from the group consisting of bis-aminomethyl dimethicone, bis-aminoethyl dimethicone, bis-aminopropyl dimethicone, bis-aminobutyl dimethicone, and mixtures thereof, wherein the lamellar gel matrix does not consists of the terminal aminosilicone
   wherein the weight ratio of total linear fatty alcohol to terminal aminosilicone is from about 0.5:1 to about 10:1
   and wherein the weight ratio of total near terminal branched alcohol to terminal aminosilicone is from about 0.5:1 to about 6:1.

2. The composition according to claim 1, wherein the weight ratio of total linear fatty alcohol to terminal aminosilicone is from about 1:1 to about 5:1.

3. Method of conditioning hair comprising applying the composition according to claim 1 onto hair.

* * * * *